(12) United States Patent
Allard et al.

(10) Patent No.: US 9,376,366 B2
(45) Date of Patent: Jun. 28, 2016

(54) METHOD FOR SYNTHESISING BIOBASED UNSATURATED ACIDS

(71) Applicants: OLEON S.A.S., Compiegne (FR); OMEGA CAT SYSTEM, Rennes (FR)

(72) Inventors: Jessica Allard, Lardy (FR); Frédéric Caijo, Thorigne Fouillard (FR); Aurélie Morel, Paris (FR)

(73) Assignees: OLEON S.A.S., Compiegne (FR); OMEGA CAT SYSTEM, Rennes (FR)

( * ) Notice: Subject to any disclaimer, the term of this patent is extended or adjusted under 35 U.S.C. 154(b) by 0 days.

(21) Appl. No.: 14/411,032

(22) PCT Filed: Jun. 27, 2013

(86) PCT No.: PCT/FR2013/051506
§ 371 (c)(1),
(2) Date: Dec. 23, 2014

(87) PCT Pub. No.: WO2014/001725
PCT Pub. Date: Jan. 3, 2014

(65) Prior Publication Data
US 2015/0336871 A1    Nov. 26, 2015

(30) Foreign Application Priority Data

Jun. 29, 2012    (FR) ...................................... 12 56280

(51) Int. Cl.
    *C07C 57/13*    (2006.01)
    *C07C 51/353*    (2006.01)
    *C07C 51/09*    (2006.01)

(52) U.S. Cl.
    CPC ............... *C07C 51/353* (2013.01); *C07C 51/09* (2013.01)

(58) Field of Classification Search
    None
    See application file for complete search history.

(56) References Cited

U.S. PATENT DOCUMENTS 5,728,917 A * 3/1998 Grubbs ................ C08G 61/128
                                                          525/938

(Continued)

FOREIGN PATENT DOCUMENTS

WO    WO 2008/065187    6/2008
WO    WO 2009/020667    2/2009

OTHER PUBLICATIONS

International Search Report for PCT/FR2013/051506, mailed Sep. 26, 2013, Lacombe, Céline, 3 pages.

(Continued)

*Primary Examiner* — Yate K Cutliff
(74) *Attorney, Agent, or Firm* — Nixon & Vanderhye P.C.

(57) ABSTRACT

The invention relates to a method for preparing a compound of formula (I),

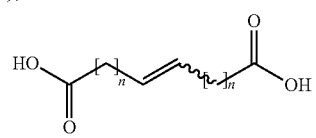

wherein
  n is an integer from 1 to 21,
  said method comprises reacting a light olefin fraction, in the presence of a metathesis catalyst, with a compound having from 10 to 24 carbon atoms, of the following formula (II):

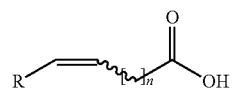

wherein,
  n is an integer from 1 to 21,
  R corresponds to a hydrogen atom or an alkyl or alkenyl chain from 1 to
  20 carbon atoms optionally substituted by at least one hydroxyl group, said compound of formula (II) being used alone or in a mixture of compounds of formula (II).

14 Claims, 5 Drawing Sheets

(56) References Cited

U.S. PATENT DOCUMENTS

| | | | |
|---|---|---|---|
| 6,803,429 B2 * | 10/2004 | Morgan | B01J 31/2226 502/155 |
| 7,754,904 B2 * | 7/2010 | Olivier-Bourbigou | C07C 1/2078 554/161 |
| 7,906,663 B2 * | 3/2011 | Olivier-Bourbigou | C07C 1/213 554/163 |
| 8,394,965 B2 | 3/2013 | Mauduit | |
| 8,586,757 B2 | 11/2013 | Mauduit | |
| 2010/0087644 A1 | 4/2010 | Mauduit | |
| 2010/0196973 A1 | 8/2010 | Dubois | |
| 2010/0305354 A1 * | 12/2010 | Dubois | C07C 51/09 560/204 |
| 2011/0105774 A1 | 5/2011 | Dubois | |
| 2013/0144060 A1 | 6/2013 | Mauduit | |

OTHER PUBLICATIONS

Ngo, H.L. et al., "Metathesis of Unsaturated Fatty Acids: Synthesis of Long-Chain Unsaturated-$\alpha,\omega$-Dicarboxylic Acids", JAOCS, vol. 83, No. 7, (2006), pp. 629-634.

Ohlmann, D.M. et al., Isomerizing Olefin Metathesis as a Strategy to Access Defined Distribusions of Unsaturated Compounds from Fatty Acids, J. Am. Chem. Soc., vol. 134, (2012), pp. 13716-13729.

* cited by examiner

METHOD FOR SYNTHESISING BIOBASED UNSATURATED ACIDS

This application is the U.S. national phase of International Application No. PCT/FR2013/051506, filed 27 Jun. 2013, which designated the U.S. and claims priority to FR Application No. 1256280, filed 29 Jun. 2012; the entire contents of each of which are hereby incorporated by reference.

The invention relates to a method for preparing a diacid, preferably a long chain diacid, by alkenolysis from a long chain fatty acid having at least one unsaturation, or from a mixture of such fatty acids. These fatty acids are preferably biobased.

The long chain diacids are used in increasingly varied fields and faced with steadily growing demand from industry. Demand is very high, especially in the field of polymers, such as polyesters, lubricants and cosmetics.

The combined industrial effort to reduce the environmental footprint and diversify supplies of diacids is growing, leading to new demand for partially or totally biobased diacids.

Generally, diacids can be produced from vegetable oils via various synthetic pathways such as fermentation, oligomerisation, oxidative cleavage, hydroformylation followed by an oxidation step and lastly olefin metathesis.

Olefin metathesis is a chemical reaction that entails a redistribution of alkylidene fragments by scission of the carbon-carbon double bond in alkenes. The reaction is catalysed by transition metals such as nickel, tungsten, rhenium, ruthenium and molybdenum. One advantage of this reaction is the very low production of by-products and hazardous waste. Yves Chauvin, Robert Grubbs and Richard R. Schrock shared the Nobel Prize in Chemistry in 2005 for the "*Development of the metathesis method in organic synthesis*". Thus, U.S. Pat. No. 5,728,917 (GRUBBS et al.) describes high performance ruthenium-based catalysts for cross-metathesis reactions in order to obtain 9-octadecenedioic acid by reacting oleic acid in the presence of ethylene and a metathesis catalyst. This method has a low diacid yield of less than 1% by weight of the composition.

Application of metathesis to vegetable oils to produce certain organic compounds has been described in particular in Foglia et al. (JAOCS, 2006, 83, 7); and the patent application published under number US2010/0196973 (Arkema).

Pathways for the synthesis of diacids remain difficult to implement and have a high production cost. A method for preparing diacids, especially octadec-9-enedioic acid, which would offer a higher yield and/or faster production, and therefore lower cost, would therefore be very advantageous.

DESCRIPTION OF THE INVENTION

The invention relates to a method for preparing a compound of formula (I),

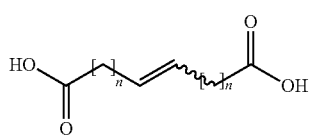

(I)

wherein
n is an integer from 1 to 21.

Said method comprises reacting a light olefin fraction, in the presence of a metathesis catalyst, with a compound having from 10 to 24 carbon atoms, of the following formula (II):

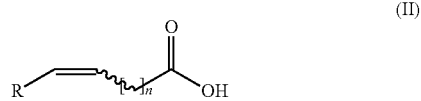

(II)

wherein,
n is an integer from 1 to 21,
R corresponds to a hydrogen atom or an alkyl or alkenyl chain from 1 to
20 carbon atoms optionally substituted by at least one hydroxyl group, said compound of formula (II) being used alone or in a mixture of compounds of formula (II).

The method according to the invention can be used to prepare diacids of formula (I) from a single compound of formula (II), i.e. from a previously purified product.

According to another embodiment of the invention, the compound of formula (II) can be used in a mixture comprising at least one other compound of formula (II).

Advantageously, the method can be used to prepare a diacid of formula (I) from a hydrolysed vegetable oil, mainly comprising a compound of formula (II) and other compounds, in particular saturated chain fatty acids, or other compounds of formula (II), such as mono-unsaturated and poly-unsaturated chain fatty acids.

"Majority compound" means a compound (II) present in a proportion of at least 50% by weight of the mixture.

This special embodiment can be used to obtain diacid compounds from vegetable oils or hydrolysed triglycerides, without the need to purify and/or separate the starting compound (II) for use in the reaction.

According to a special embodiment of the invention, a diacid of formula (I) is prepared from a purified hydrolysed oil, comprising a compound of formula (II) present in a proportion of more than 80% of the mixture.

The compound of formula (II) is preferably a long chain natural fatty acid. Long chain natural fatty acid means an acid of animal or vegetable origin, including algae, especially from the vegetable kingdom and therefore readily renewable.

Advantageously, the compound of formula (II) has at least 12 carbon atoms and more preferably, at least 14 carbon atoms.

We may mention for example the C10 acids, such as obtusilic acid (cis-4-decenoic) and caproleic acid, the C12 acids, such as lauroleic acid (cis-5-dodecenoic) and linderic acid (cis-4-dodecenoic), the C14 acids, such as myristoleic acid (cis-9-tetradecenoic), physeteric acid (cis-5-tetradecenoic) and tsuzuic acid (cis-4-tetradecemoic), the C16 acids, such as palmitoleic acid (cis-9-hexadecenoic), the C18 acids, such as oleic acid (cis-9-octadecenoic), elaidic acid (trans-9-octadecenoic), petroselinic acid (cis-6-octadecenoic), vaccenic acid (cis-11-octadecenoic) and ricinoleic acid (12-hydroxy-cis-octadecenoic), the C20 acids, such as gadoleic acid (cis-9-eicosenoic), gondoic acid (cis-11-eicosenoic), cis-5-eicosenoic acid and lesquerolic acid (14-hydroxy-cis-11-eicosenoic), the C22 acids, such as cetoleic acid (cis-11-docosenoic) and erucic acid (cis-13-docosenoic).

Preferably, the fatty acids used are oleic acid (cis-9-octadecenoic), myristoleic acid (cis-9-tetradecenoic), palmitoleic acid (cis-9-hexadecenoic), elaidic acid (trans-9-octadecenoic acid), ricinoleic acid (12-hydroxy-cis-9-octadecenoic), gadoleic acid (cis-9-eicosenoic) or erucic acid.

According to a particularly preferred embodiment of the invention, the acid of formula (II) is oleic acid.

Preferably, the poly-unsaturated chain fatty acid is selected from linoleic acid and linolenic acid.

For example, a saturated chain fatty acid may be palmitic acid (C16) or stearic acid (C18).

The fatty acids which can be used as substrates in the method of the invention are advantageously biobased and may for example be obtained from rapeseed, sunflower, soya bean, oleic sunflower, castor, safflower, coconut, palm, tallow, olive, cotton, linseed, corn, tung, peanut, calendula or grapeseed oil.

According to a preferred embodiment of the invention, the catalyst used is selected from the group of metathesis reaction catalysts based on ruthenium, tungsten or molybdenum, possibly based on osmium, chromium and/or rhenium and/or any other metals selected from groups 6, 7 and 8 of the Periodic Table of Elements. Catalysts suitable for cross-metathesis reactions of fats are known to those skilled in the art and a list of acceptable catalysts is given for example in document WO2009/020667 (pages 18 to 46) and document WO2008/065187 (pages 29 to 36) which are incorporated by reference. Thus, catalysts particularly suitable for implementing the method according to the invention are for example ruthenium-based first and second generation Grubbs catalysts.

A catalyst especially suitable for producing the required yields is the catalyst of formula D:

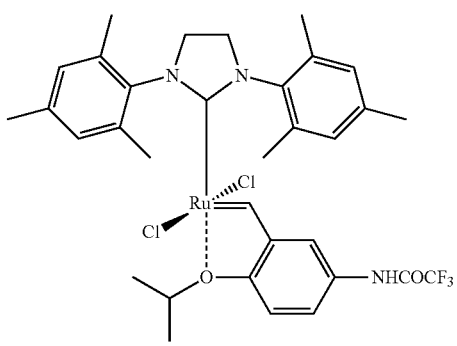

a-2F (M71). This catalyst is available from Umicore (Belgium) under the name M71-SiPr.

Another catalyst especially suitable for producing the required yields is the catalyst of formula E:

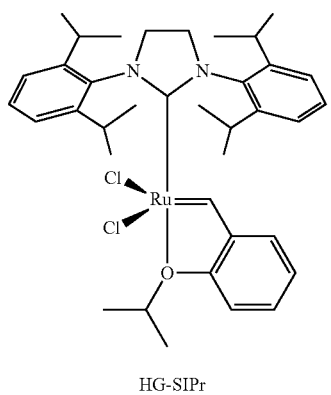

HG-SIPr

This catalyst is available from Materia Inc. (United States) under the name HG-SIPr (Hoveyda-Grubbs SIPr).

As demonstrated in the examples, these catalysts can be used to obtain particularly advantageous yields.

The catalyst used in this reaction may be supported or unsupported. Various supports can be used during this reaction and can be selected from the group consisting of resins, polymers, PEGs or silica gels having a surface or terminal amino, hydroxy, alkylthio, haloalkyl or carboxylic group. Carbon nanotubes and biopolymers are also possible supports.

Catalysis can be conducted in the presence or absence of solvent and/or ionic liquid. The ionic liquids possibly used during this reaction are selected from the group consisting of liquid salts of general formula $Q^+A^-$ wherein $Q^+$ represents a quaternary phosphonium, a quaternary ammonium, a quaternary guanidinium or a quaternary sulphonium and $A^-$ represents an anion which is capable of forming a liquid salt below 90° C.

The catalyst may be added either as a solution in an organic solvent (e.g. dichloromethane), or in powder form in the initial reaction mixture. Moreover, the catalyst can be added either sequentially, for example in two stages, or continuously to the reaction medium.

This reaction is preferably conducted in the absence of solvent and/or of ionic liquid.

A light olefin fraction means at least one compound selected from a range of unsaturated hydrocarbons containing at least one double bond and having from 2 to 10 carbon atoms, preferably from 2 to 5 carbon atoms.

This compound is preferably selected from the group consisting of ethylene, propylene, 1-butene, 2-butene, isobutene, 1-pentene, 2-pentene, 3-pentene, 2-methyl-1-butene, 2-methyl-2-butene, 3-methyl-1-butene, cyclopentene and a mixture thereof. Ethylene is particularly suitable for the method according to the invention.

The method according to the invention can be used to obtain high yields (e.g. at least 60% by weight of compound (I)), in a short reaction time, for example less than or equal to 10 hours and preferably less than 6 hours. Preferably, at least 60% by weight of compound (I) is obtained, in a reaction time less than or equal to 4 hours, preferably less than 2 hours.

Advantageously, at least 70% by weight of compound (I) is obtained in 2 hours, more preferably 72% by weight of compound (I).

According to a preferred embodiment, the reaction is conducted at a temperature ranging from 44° C. to 120° C. Preferably, the temperature will be selected in the range from 45° C. to 80° C., preferably from 45° C. to 65° C. and more preferably in the range from 48° C. to 55° C. Advantageously, the reaction is conducted at a temperature of about 50° C., i.e. 50° C.±1° C.

The reaction temperature is advantageously selected to be less than or equal to the temperature at which the diacid, or compound of formula (I), precipitates. Moreover, it is also advantageous to select this temperature so that it is greater than or equal to the melting point of the compound of formula (II), majority compound in the starting mixture, and/or of the reaction by-products. Within this temperature range, the diacid can be precipitated selectively and quickly while maintaining the other compounds of the reaction mixture in soluble form. This helps to shift the reaction equilibrium in the desired direction.

For example, if the substrate is oleic acid, the reaction must be conducted at a temperature greater than the melting point of elaidic acid (42° C. to 44° C.). Elaidic acid is a monoacid of E configuration which is a by-product of the metathesis reaction between 1-decene and dec-9-enoic acid which are themselves the alkylidene fragments obtained by scission of the carbon-carbon double bond in oleic acid (see FIG. 1). The reaction must also be conducted at a temperature advantageously selected to be less than the melting point of octadec-9-enedioic acid (E), i.e. at a temperature of less than 98° C. in order to keep the required diacid in solid state. These temperatures correspond to the limiting temperatures related to the physicochemical characteristics of the compounds involved. A reaction temperature of about 50° C. is therefore particularly suitable for the synthesis of octadec-9-enedioic acid (E).

If the starting compound (II) is erucic acid, the reaction must preferably be conducted at a temperature greater than the melting point of brassidic acid, the isomer (E) of erucic acid, which is about 58° C., and below the melting point of the diacid (E) (acid 1,26-hexacos-13-enedioic acid) at about 95° C. to 110° C. A temperature ranging from 65° C. to 85° C. is therefore suitable for this particular aspect of the invention.

According to another preferred embodiment of the method according to the invention, the light olefin fraction is reacted in gaseous form and/or at a pressure of between atmospheric pressure and 100 bar. Preferably, the pressure of the light olefin fraction is from 2 bar to 30 bar, and more preferably from 5 bar to 20 bar, for example 10 bar. Even more preferably, the light olefin fraction is reacted at a pressure of 1 bar to 3 bar. Advantageously, it is from 1.5 bar to 2.5 bar, more preferably from 1.7 bar to 2.3 bar, the pressure is typically 2 bar+/−1 bar.

Preferably, the method can be used to obtain a majority of the compound in trans configuration.

According to a preferred embodiment of the invention, the compound of formula (I) obtained by the method according to the invention is octadec-9-enedioic acid, which is obtained by reacting oleic acid with ethylene, in the presence of a metathesis catalyst preferably ruthenium, at a temperature preferably selected in the range from 45° C. to 65° C., and more particularly from 49° C. to 52° C. (e.g. 50° C.), and at an ethylene pressure preferably selected in the range from either 5 bar to 20 bar, or from 1 bar to 3 bar (for example 2 bar). According to this preferred embodiment, the synthesis is completed in less than 10 hours, and preferably in about 2 hours.

According to another embodiment, the method according to the invention can be used in an integrated method for the synthesis or diacid or compound of formula (I). This method comprises at least one preliminary step consisting in transforming a triglyceride, such as a vegetable oil, into an acid of formula (II) by hydrolysis reaction and/or in pretreating the product of a hydrolysis reaction conducted on triglycerides, for example, to eliminate or reduce certain impurities.

Optionally, the method according to the invention may comprise a step for purifying the diacid obtained.

A diagram showing these associated steps in an integrated method is shown in FIG. 3.

Hydrolysis of triglycerides to obtain fatty acids is a known reaction which is conducted by subjecting the triglycerides to a treatment with sodium hydroxide.

Pretreatment of the hydrolysis product is an advantageous step which improves the efficiency of the metathesis reaction. The fatty acids obtained by hydrolysis of vegetable oils contain impurities, especially peroxides, which can act as poisons for ruthenium-based olefin metathesis catalysts. The presence of these impurities in the fatty acids depends on several factors including the plant from which the oil is extracted, the geographic origin, the harvesting date, the extraction method and the hydrolysis method.

Selective pretreatments may therefore be applied to reduce the content of impurities, especially peroxide, to less than 1 mEq/kg, preferably to less than 0.5 mEq/kg.

The pre-treatments most commonly used to eliminate or reduce certain impurities are summarised in Table 1 below:

| Treatment | Impurity |
|---|---|
| Filtration | Salts and solids |
| Bubbling with an inert gas | Oxygen |
| Heat treatment alone, preferably >100° C. | Peroxides (<1 mEq/kg) |
| Chemical treatment, preferably with sodium bisulphite | Peroxides (<1 mEq/kg) |
| Chemical treatment, preferably with sodium borohydride | Peroxides (<1 mEq/kg) |
| Flash distillation | Light organic compounds and water |

Firstly, the solid particles can be removed by decantation and/or by filtration on 60 μm to 5 μm filters, preferably 10 μm to 5 μm filters.

Vacuum or nitrogen bubbling degassing can be conducted to remove traces of oxygen.

The fatty acids can be heat and/or chemically treated to eliminate the impurities likely to reduce the efficiency of the catalysts used, for example in particular: peroxides, glycerol, water, aldehydes, alcohols, by-products related to oxidative degradation of fatty acids, terminal conjugated polyolefins, nitriles and other coloured impurities such as indane, naphthalene, phenanthrene, pyrene and alkylbenzenes.

Heat treatment is generally carried out at a temperature ranging from 30° C. to 200° C., preferably from 50° C. to 180° C. and for a time depending on the content of impurities to be eliminated. This heat treatment can be conducted at reduced pressure to increase its efficiency.

Chemical treatment of the triglyceride hydrolysis product can be conducted using sodium bisulphite and/or sodium borohydride.

Sodium bisulphite is known to reduce peroxides into aldehydes and form water-soluble compounds with them. Sodium bisulphite in aqueous solution can be added to the composition in a proportion of from 5% to 0.1% by weight, advantageously from 0.5% to 0.1% by weight. The sodium bisulphite is then removed from the medium by aqueous treatment.

Sodium borohydride is known to reduce peroxides into aldehydes then into alcohols. Its use in the pretreatment of fatty acid compositions can also remove coloured impurities or glycerol derived from hydrolysis of the oil. Sodium borohydride can be added to the vegetable oil in a proportion of from 5% to 0.1% by weight and preferably from 0.5% to 0.1% by weight. Sodium borohydride is then removed from the medium by aqueous treatment.

The aqueous phase is, in turn, then removed by decantation, centrifuging or by any other liquid-liquid separation means.

The residual traces of water can then be removed by flash distillation, which consists in vaporising the residual traces of water and in obtaining two phases in liquid-vapour equilibrium at the flash temperature and pressure.

The invention also relates to the diacids produced directly by the method as described above and to their industrial and cosmetic applications.

BRIEF DESCRIPTION OF THE DRAWINGS

The invention will be better understood on reading the following description, given solely by way of example and with reference to the figures wherein.

EXAMPLE 1

Synthesis of octadec-9-enedioic acid

Figure 1:
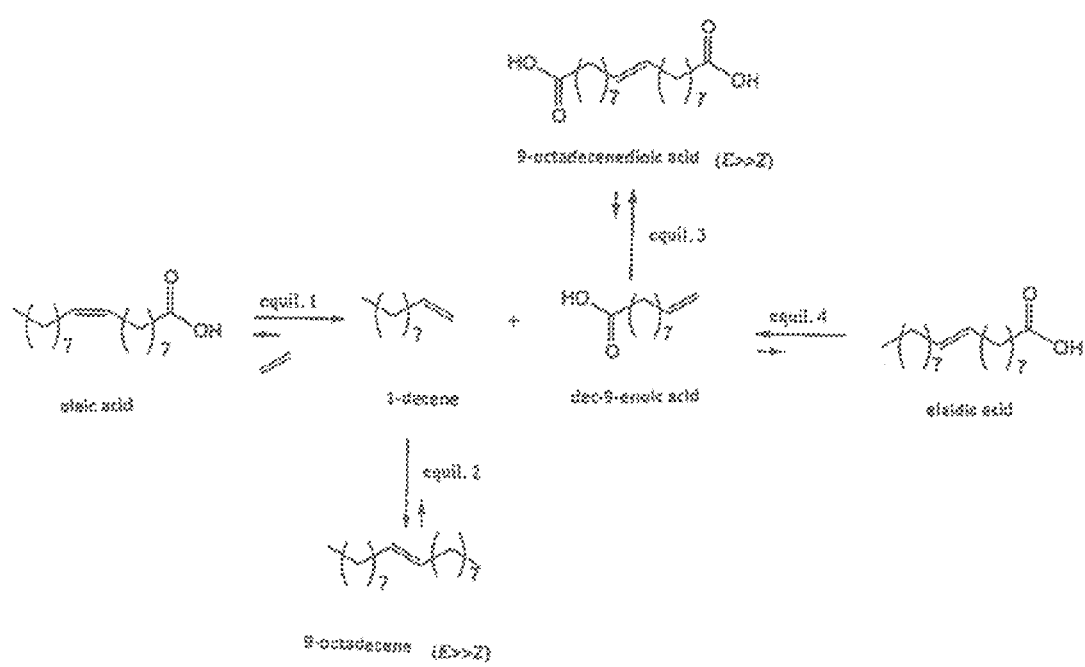
FIG. 1 represents the reaction scheme of the reaction conducted in example 1.
Figure 2A:
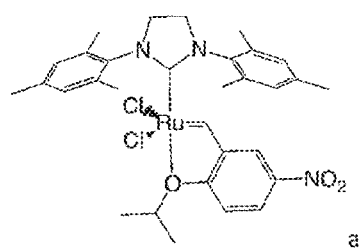
FIG. 2 represents a non-exhaustive list of the structure of the catalysts that can be used to implement the invention (FIG. 2A, FIG. 2B, FIG. 2C, FIG. 2D, FIG. 2E, FIG. 2F, FIG. 2G, FIG. 2H)
Figure 2B:
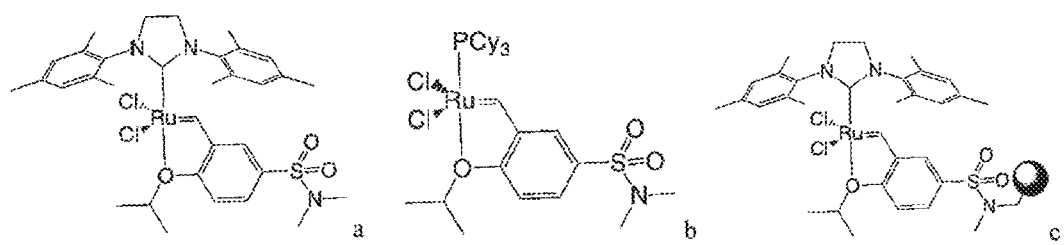
Figure 2C:
Figure 2D:
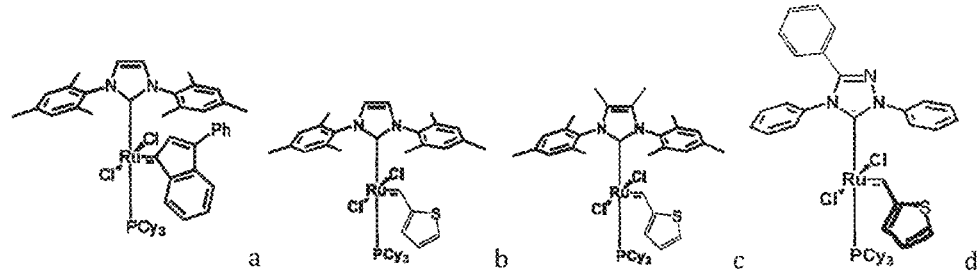
Figure 2E:
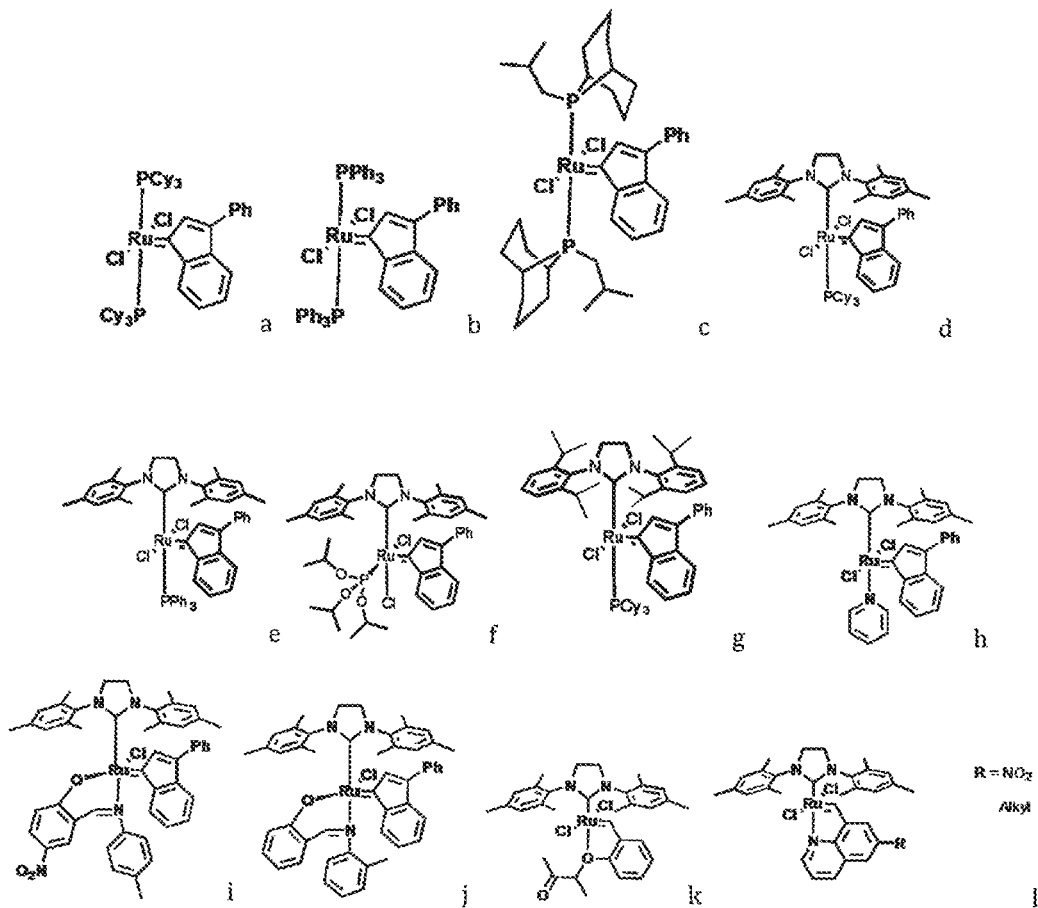
Figure 2F:
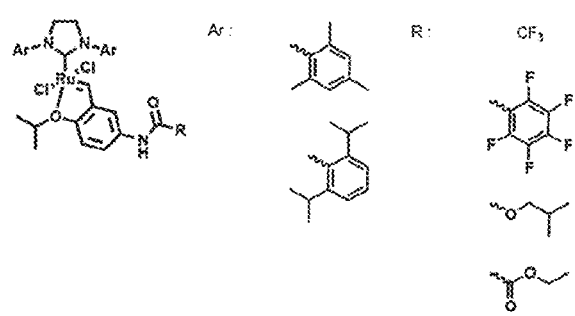
Figure 2G:
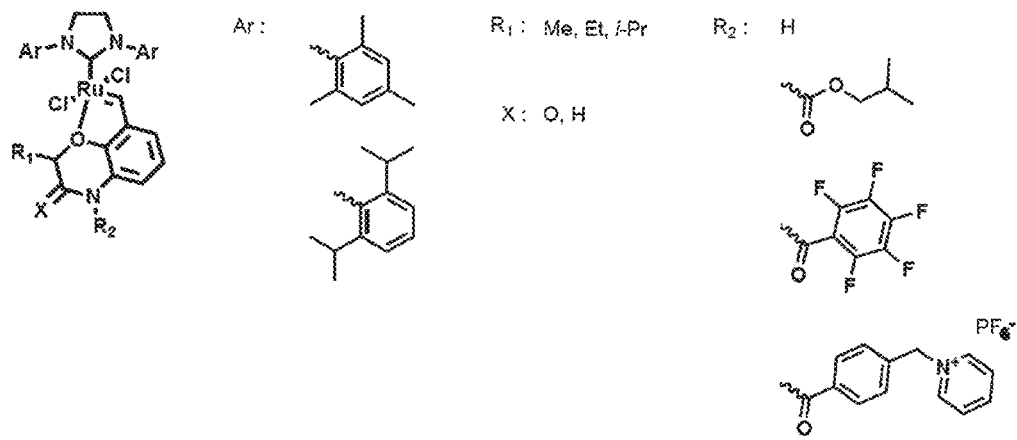
Figure 2H:
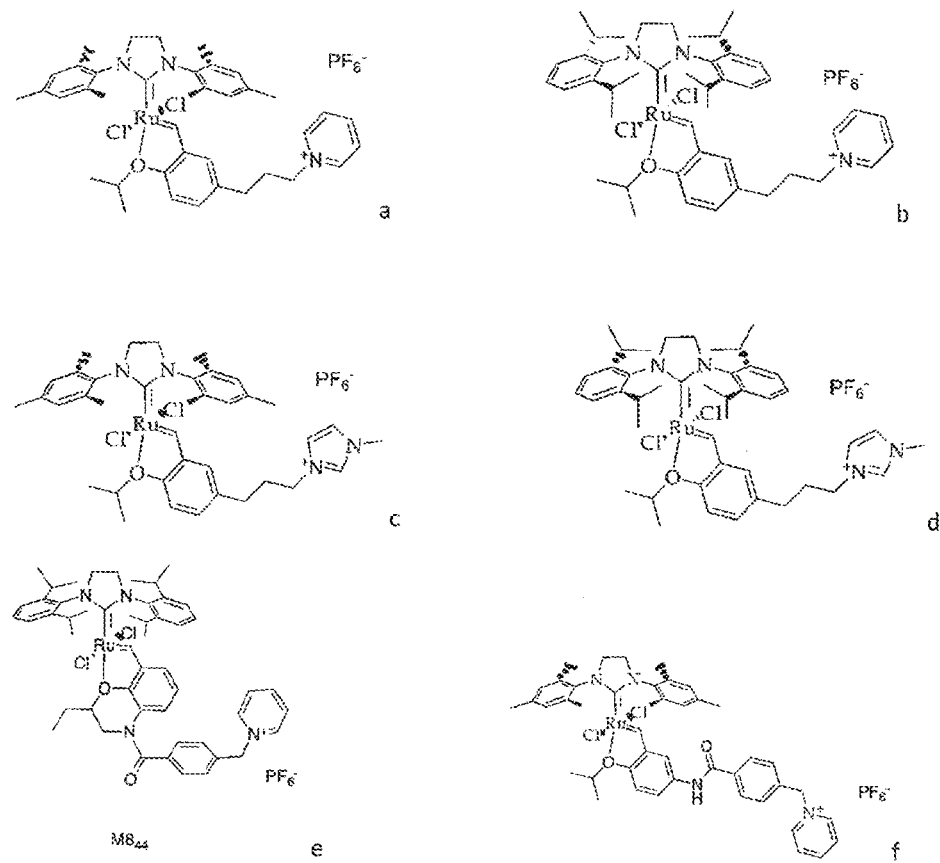
Figure 3:
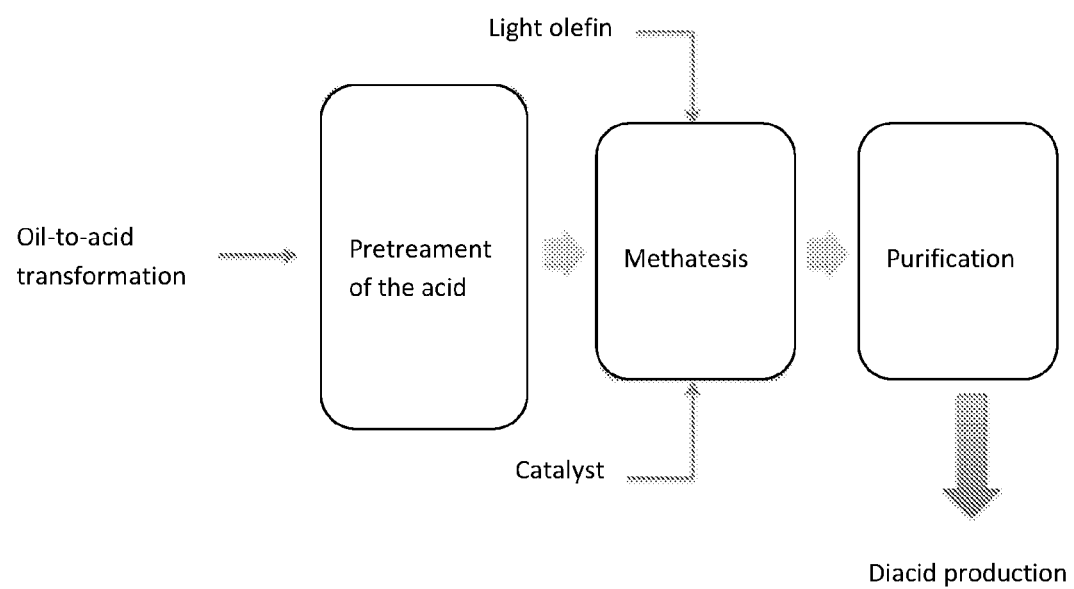
FIG. 3 represents the diagram of an integrated method for the synthesis of diacids described previously.

Compounds Used:
oleic acid whose composition determined by gas chromatography is given in Table 1,
ethylene, and
ruthenium-based catalyst of type M71-SIPr.

TABLE 1

| % area | Oleic acid (90%) |
|---|---|
| Unknown peak of retention time 1.32 min | 0.85 |
| Methyl palmitate | 1.98 |
| Methyl oleate + linoleate + linolenate | 89.36 |
| Methyl stearate | 1.83 |
| Other products | 5.98 |

% area = chromatographic peak

Protocol:
10 g of 90% pure oleic acid (11.2 mL; 31.86 mmol) are placed in an autoclave heated to a temperature of 50° C., in the presence of 26 mg of catalyst (31.9 µmol; 0.1 mol %). The autoclave is closed and pressurised to an ethylene pressure of 10 bar. The reaction medium is stirred for 2 hours.

The catalyst is destroyed by adding 1 mL of ethyl vinyl ether.

The solid thus obtained is filtered and washed with two successive additions of 20 mL of cyclohexane. It is then heated to 60° C. in suspension in 20 mL of hexane, hot filtered and washed with 20 mL of hot hexane.

Lastly, the solid is dried using a vacuum pump at 60° C. for 3 hours.

3.58 g of a white powder with a melting point of 95° C. to 96° C. (lit.: 98° C. to 99° C.) are obtained.

The proton NMR analysis shows that the mass yield of the reaction is 72% and that the solid has only 7 mol % of dec-9-enoic acid.

EXAMPLE 2

Synthesis of octadec-9-enedioic acid

Compounds Used:
90% pure oleic acid,
ethylene, and
ruthenium-based catalyst of type M71-SIPr.
Protocol:
10 g of 90% pure oleic acid (11.2 mL; 31.86 mmol) are placed in an autoclave heated to a temperature of 50° C., in the presence 0.1 mol % of catalyst M71-SIPr. The autoclave is closed and pressurised to an ethylene pressure of 2 bar. The reaction medium is stirred for 2 hours.

The catalyst is destroyed by adding 1 mL of ethyl vinyl ether.

The solid thus obtained is filtered and washed with two successive additions of 20 mL of cyclohexane. It is then heated to 60° C. in suspension in 20 mL of hexane, hot filtered and washed with 20 mL of hot hexane.

Lastly, the solid is dried using a vacuum pump at 60° C. for 3 hours.

The weight percentages of the compounds forming the solid obtained are as follows:

TABLE 2

| | wt % M71-SIPr |
|---|---|
| 1-decene | 1.6 |
| 9-DA | 4 |
| 9-octadecene | 19 |
| Oleic acid | 3.9 |
| Elaidic acid | 20.1 |
| D18:1 Z | 2.7 |
| D18:1 E | 38.1 |
| D18:1 total | 40.8 |

The proton NMR analysis shows that the mass yield of the reaction is 76.6%.

EXAMPLE 3

Synthesis of octadec-9-enedioic acid

Compounds Used:
90% pure oleic acid,
ethylene, and
ruthenium-based catalyst of type HG-SIPr.

The protocol of example 2 is repeated identically with the catalyst HG-SIPr.

The weight percentages of the compounds forming the solid obtained are as follows:

TABLE 3

| | wt % HG-SIPr |
|---|---|
| 1-decene | 3.5 |
| 9-DA | 6.4 |
| 9-octadecene | 14.9 |
| Oleic acid | 3 |
| Elaidic acid | 17.7 |
| D18:1 Z | 2.5 |
| D18:1 E | 35.8 |
| D18:1 total | 38.3 |

The proton NMR analysis shows that the mass yield of the reaction is 81.6%.

The invention claimed is:
1. A method for preparing a compound of formula (I),

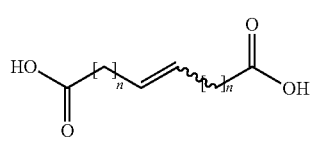

wherein
n is an integer from 1 to 21,
said method comprises reacting a light olefin fraction, in the presence of a metathesis catalyst, with a compound having from 10 to 24 carbon atoms, of the following formula (II):

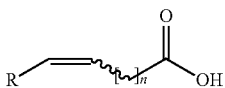

(II)

wherein, n is an integer from 1 to 21,

R corresponds to a hydrogen atom or an alkyl or alkenyl chain from 1 to 20 carbon atoms optionally substituted by at least one hydroxyl group, said compound of formula (II) being used alone or in a mixture of compounds of formula (II), and the reaction is conducted at a temperature ranging from 44° C. to 120° C., wherein said catalyst is selected from the group consisting of the following catalysts:

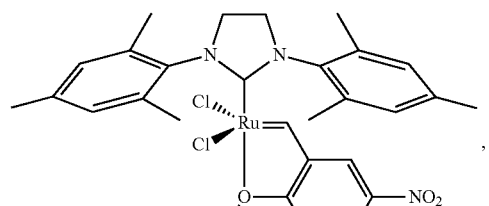

,

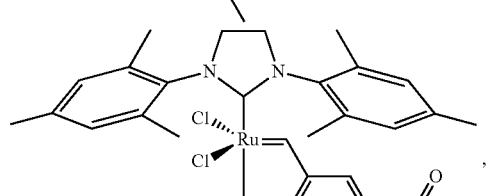

,

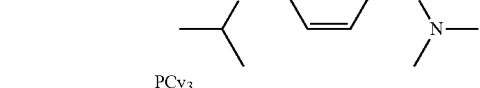

,

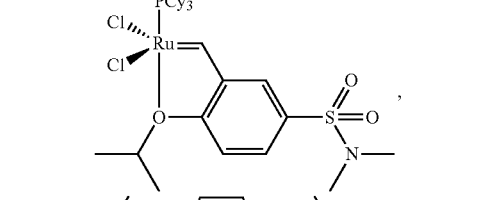

,

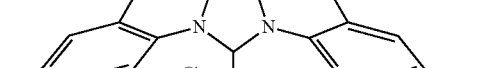

,

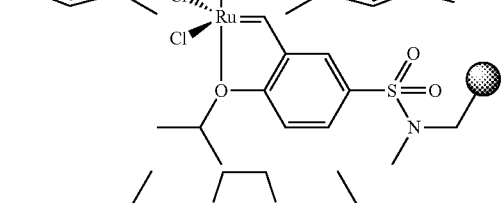

,

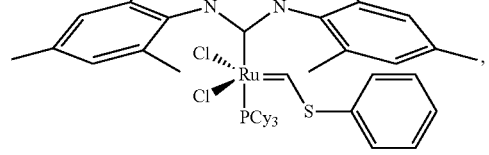

-continued

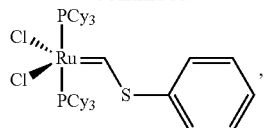

,

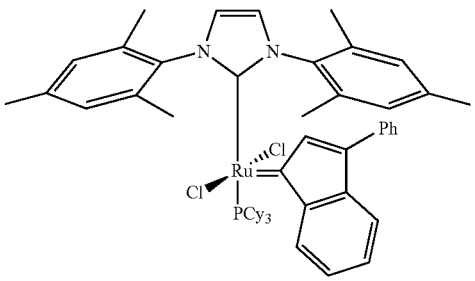

,

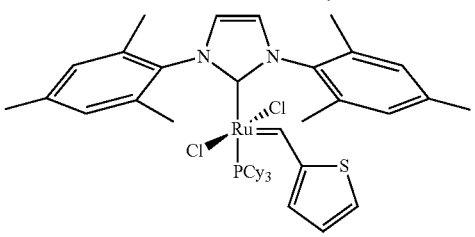

,

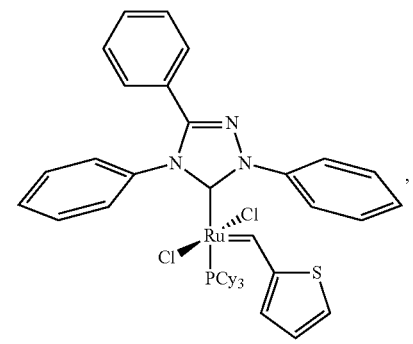

,

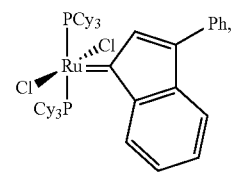

,

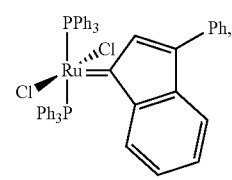

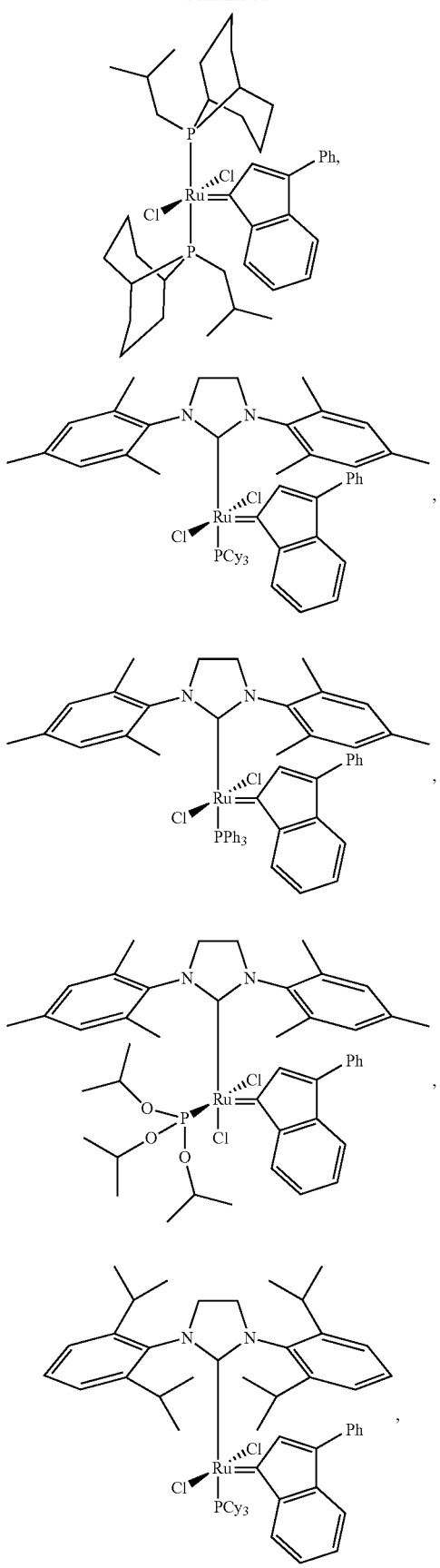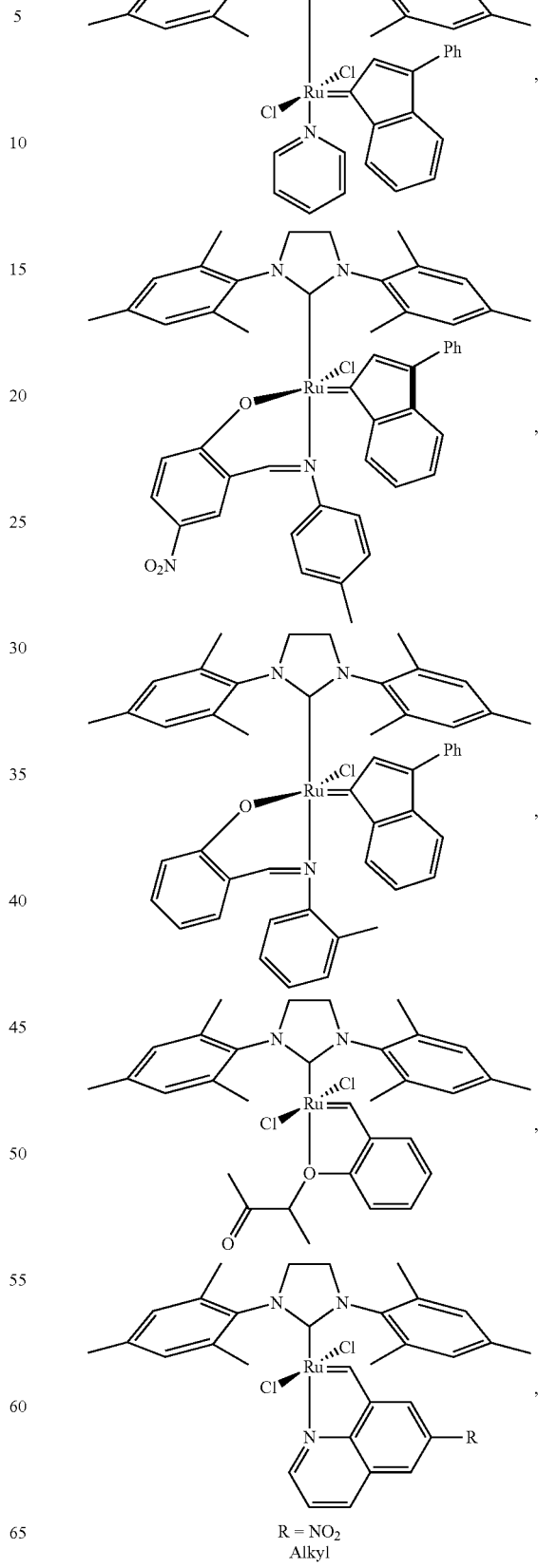

13
-continued
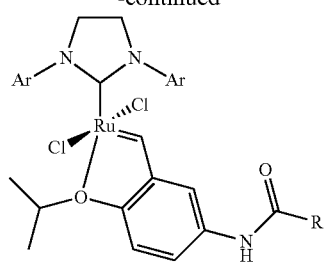
Ar: 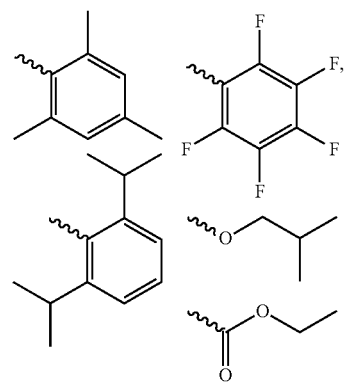  R: CF₃
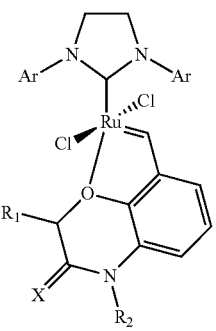
Ar: 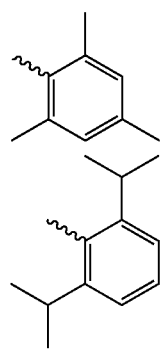  R₁: Me, Et, i-Pr  R₂: H
X: O, H
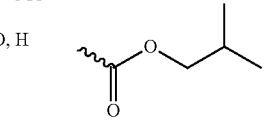
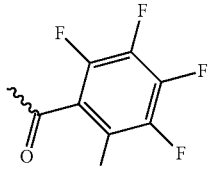
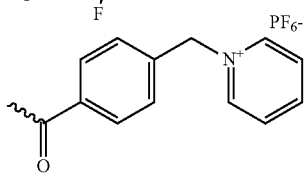
14
-continued
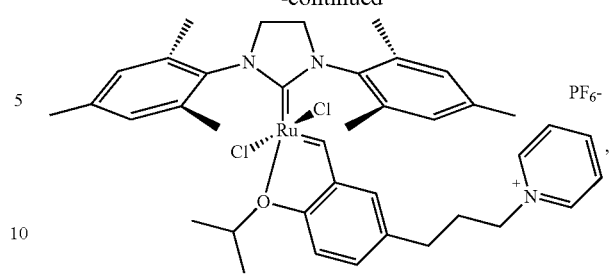 PF₆⁻,
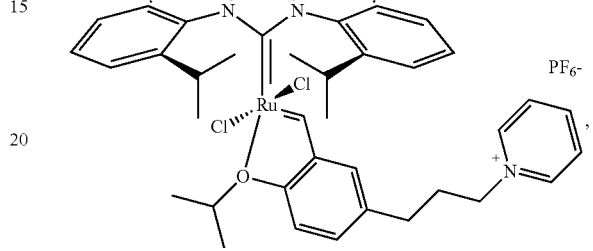 PF₆⁻,
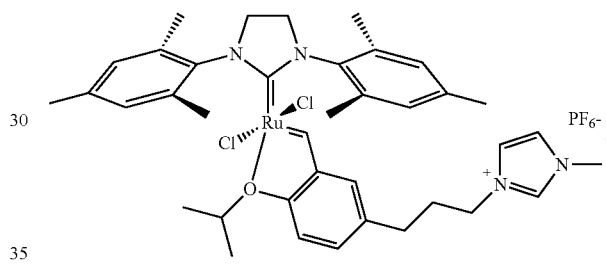 PF₆⁻,
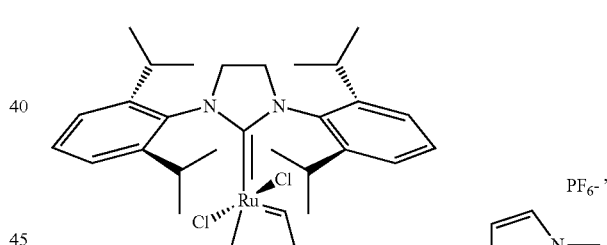 PF₆⁻,
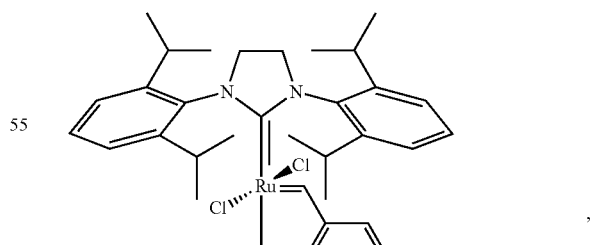
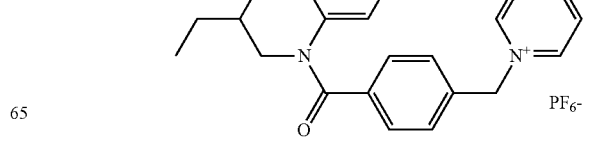 PF₆⁻

-continued

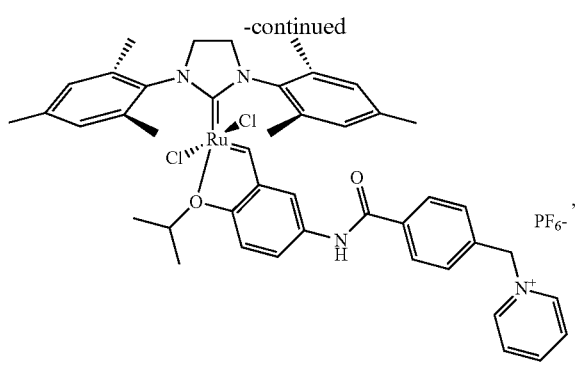

and a mixture thereof.

2. The method according to claim 1, wherein the light olefin fraction is reacted in gaseous form.

3. The method according to claim 1, wherein the light olefin fraction is reacted at pressure ranging from atmospheric pressure to 100 bar.

4. The method according to claim 1, wherein the light olefin fraction is reacted at a pressure ranging from 1 bar to 3 bar.

5. The method according to claim 1, wherein only one compound of formula (II) is used in the reaction.

6. The method according to claim 1, wherein the compound of formula (II) is used in a mixture comprising, in addition, at least one other compound of formula (II).

7. The method according to claim 1, wherein the compound of formula (II) is obtained from rapeseed, sunflower, soya bean, oleic sunflower, castor, safflower, coconut, palm, tallow, olive, cotton, linseed, corn, tung, peanut, calendula or grapeseed oil.

8. The method according to claim 1, wherein the compound of formula (II) is oleic acid.

9. The method according to claim 1, wherein the light olefin fraction is selected from the group consisting of ethylene, propylene, 1-butene, 2-butene, isobutene, 1-pentene, 2-pentene, 3-pentene, 2-methyl-1-butene, 2-methyl-2-butene, 3-methyl-1-butene, cyclopentene and a mixture thereof.

10. The method according to claim 9, wherein the light olefin fraction is ethylene.

11. The method according to claim 1, wherein the reaction is conducted at a temperature of 50° C.

12. The method according to claim 1, used to obtain at least 60% by weight of compound (I), in a reaction time less than or equal to 6 hours.

13. The method according to claim 1, wherein the compound of formula (I) is octadec-9-enedioic acid.

14. The method according to claim 1, wherein the compound of formula (II) is obtained by conducting at least one of the following preliminary steps:
hydrolyse a compound comprising triglycerides into fatty acids, and
treat the product of a triglyceride hydrolysis reaction by filtration, bubbling, heat treatment, chemical treatment and/or flash distillation.

* * * * *